US012600952B2

(12) United States Patent
Stoddart et al.

(10) Patent No.: US 12,600,952 B2
(45) Date of Patent: Apr. 14, 2026

(54) METHOD OF DETERMINING OR INFLUENCING THE CHONDROGENIC POTENTIAL OF MESENCHYMAL STROMAL CELLS

(71) Applicant: AO TECHNOLOGY AG, Chur (CH)

(72) Inventors: Martin Stoddart, Davos Dorf (CH); Mauro Alini, Porto Ronco (CH)

(73) Assignee: AO TECHNOLOGY AG, Chur (CH)

( * ) Notice: Subject to any disclaimer, the term of this patent is extended or adjusted under 35 U.S.C. 154(b) by 889 days.

(21) Appl. No.: 17/597,269

(22) PCT Filed: Jul. 3, 2020

(86) PCT No.: PCT/EP2020/068848
§ 371 (c)(1),
(2) Date: Dec. 30, 2021

(87) PCT Pub. No.: WO2021/001542
PCT Pub. Date: Jan. 7, 2021

(65) Prior Publication Data
US 2022/0315896 A1 Oct. 6, 2022

(30) Foreign Application Priority Data
Jul. 3, 2019 (EP) ..................................... 19184241

(51) Int. Cl.
*C12N 5/077* (2010.01)
*C07K 14/705* (2006.01)
(52) U.S. Cl.
CPC .......... *C12N 5/0655* (2013.01); *C07K 14/705* (2013.01); *C12N 2501/15* (2013.01); *C12N 2506/1353* (2013.01)
(58) Field of Classification Search
CPC .............. C12N 5/0655; C12N 2501/15; C12N 2506/1353; C12N 2510/00; C07K 14/705
See application file for complete search history.

(56) References Cited

FOREIGN PATENT DOCUMENTS

KR 10-2012-0096150 A 8/2012
KR 20120096150 A * 8/2012 ........... C12N 5/0655

OTHER PUBLICATIONS

Jongchan Ahn, et al., "Transplantation of human Wharton's jelly-derived mesenchymal stem cells highly expressing TGFβ receptors in a rabbit model of disc degeneration", Stem Cell Research & Therapy, Oct. 2, 2015, pp. 1-13, vol. 6, No. 1.
Sun-Woong Kang, et al., "Increase of chondrogenic potentials in adipose-derived stromal cells by co-delivery of type I and type II TGFβ receptors encoding bicistronic vector system", Journal of Controlled Release, Jun. 1, 2012, pp. 577-582, vol. 160, No. 3.
Shuhui Zheng, et al., "Type III Transforming Growth Factor-β Receptor RNA Interference Enhances Transforming Growth Factor β3-Induced Chondrogenesis Signaling in Human Mesenchymal Stem Cells", Stem Cells International, Aug. 8, 2018, pp. 1-11, vol. 2018.
Valeria Graceffa, et al., "Chasing Chimeras—The elusive stable chondrogenic phenotype", Biomaterials, Feb. 1, 2019, pp. 199-225, vol. 192.
Rene Rothweiler, et al., "Predicting and Promoting Human Bone Marrow MSC Chondrogenesis by Way of TGFβ Receptor Profiles: Toward Personalized Medicine", Frontiers in Bioengineering and Biotechnology, Jun. 26, 2020, pp. 1-13, vol. 8.
International Search Report for PCT/EP2020/068848 dated Sep. 7, 2020 (PCT/ISA/210).
Written Opinion for PCT/EP2020/068848 dated Sep. 7, 2020 (PCT/ISA/237).

* cited by examiner

*Primary Examiner* — Jeremy C Flinders
*Assistant Examiner* — Masudur Rahman
(74) *Attorney, Agent, or Firm* — Sughrue Mion, PLLC

(57) ABSTRACT

A method of increasing the chondrogenic potential mediated by TGFβ of a mesenchymal stromal cell (MSC) or a population of mesenchymal stromal cells (MSCs), comprising the step of increasing the amount of TGFβR1, and/or decreasing the amount of TGFβR2, and/or decreasing the amount of and/or ACVRL1 of the MSC or a population of mesenchymal stromal cells (MSCs).

23 Claims, 7 Drawing Sheets

Specification includes a Sequence Listing.

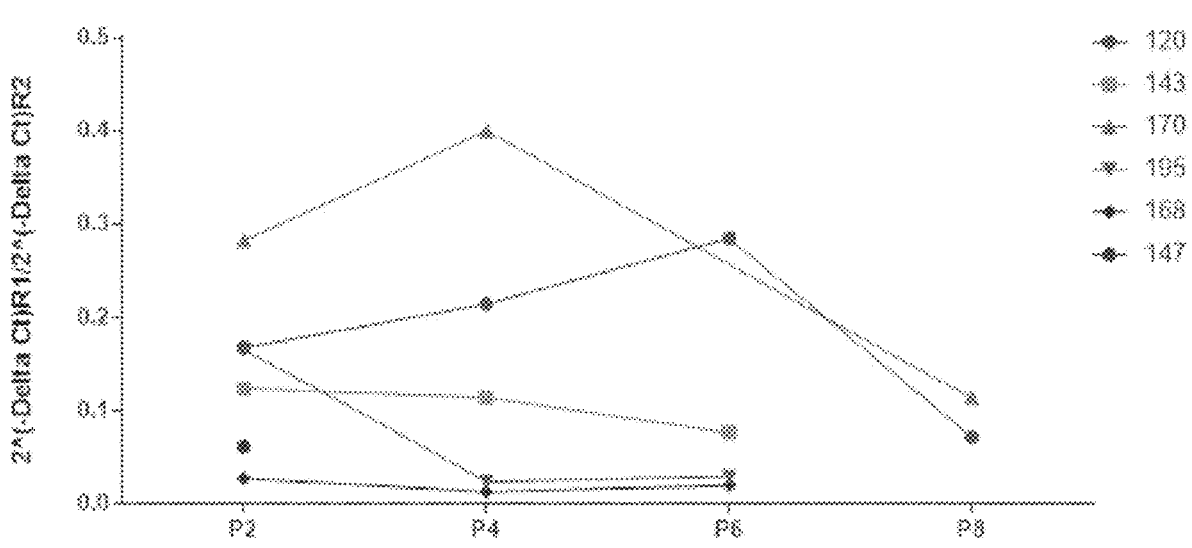
FIG. 1
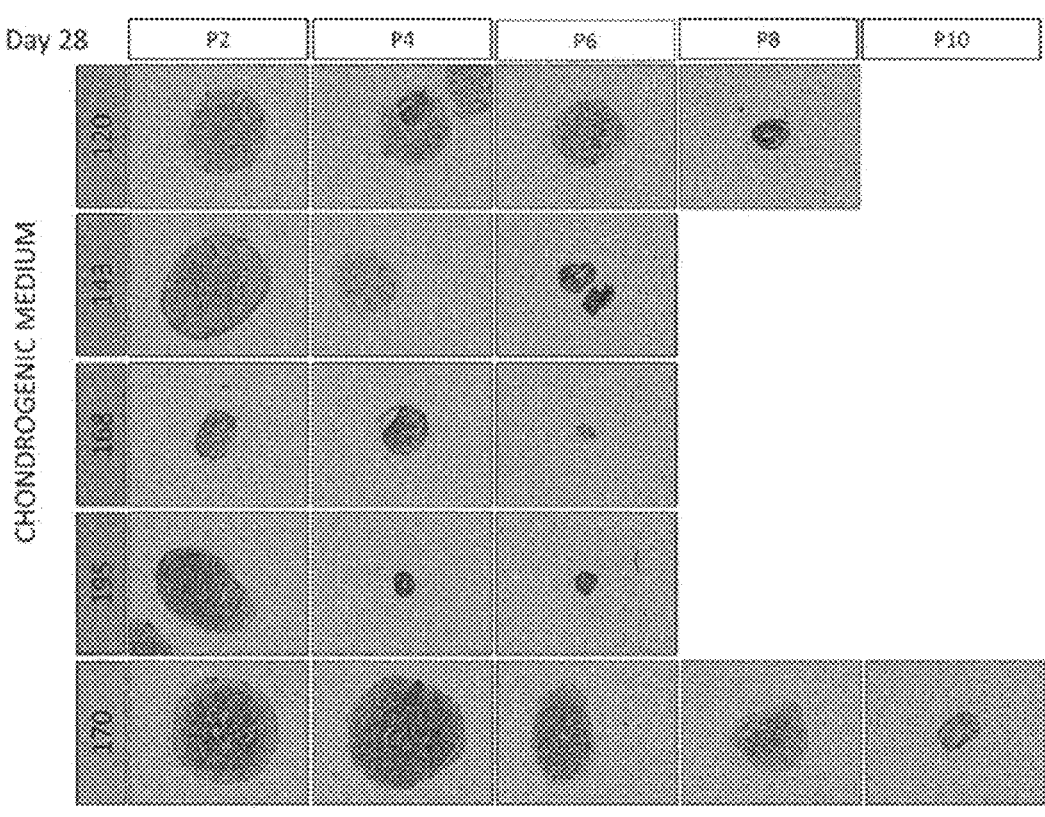
FIG. 2

FIG. 3

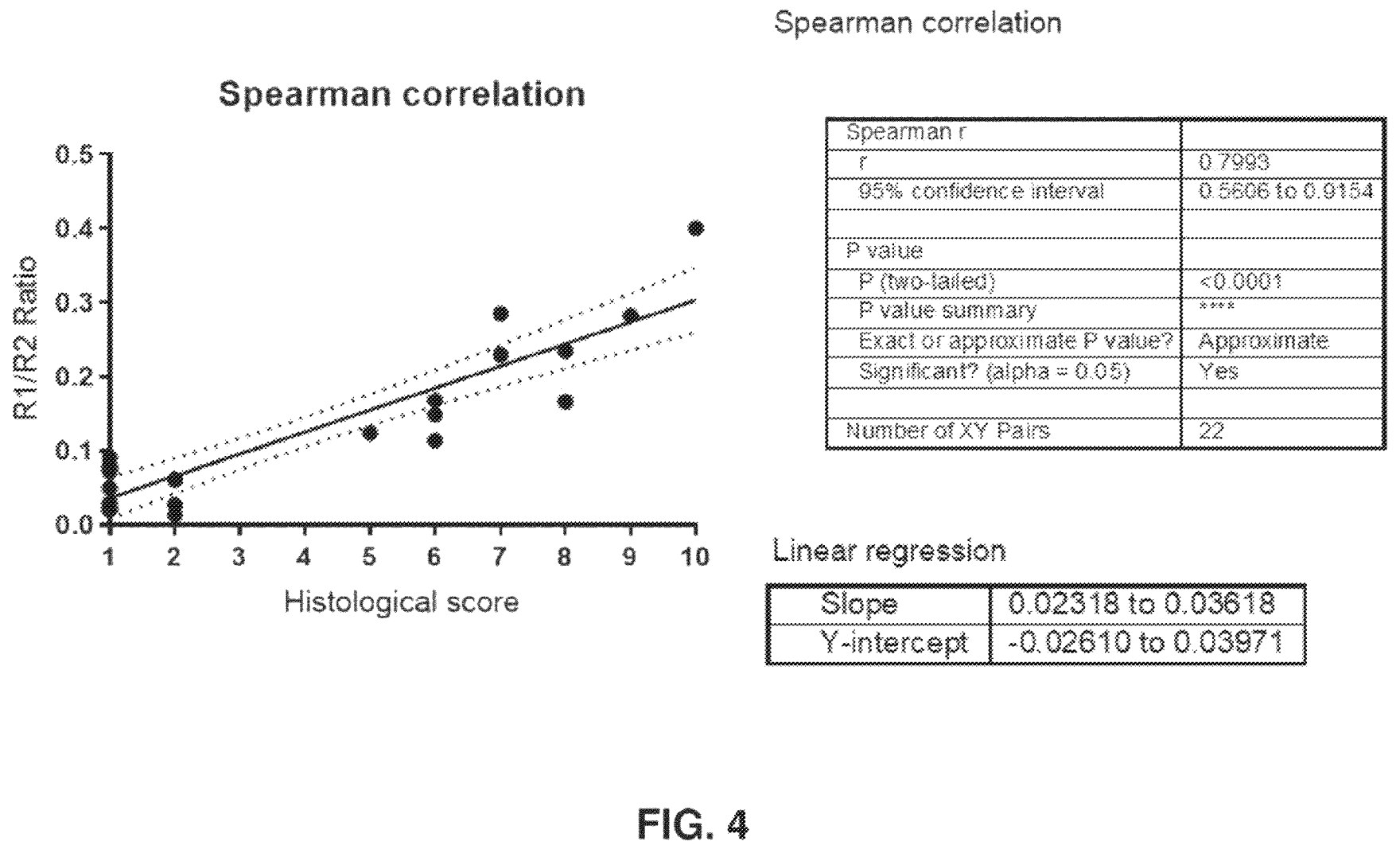

Spearman correlation

| Spearman r | |
|---|---|
| r | 0.7993 |
| 95% confidence interval | 0.5506 to 0.9154 |
| P value | |
| P (two-tailed) | <0.0001 |
| P value summary | *** |
| Exact or approximate P value? | Approximate |
| Significant? (alpha = 0.05) | Yes |
| Number of XY Pairs | 22 |

Linear regression

| Slope | 0.02318 to 0.03618 |
|---|---|
| Y-intercept | -0.02610 to 0.03971 |

Spearman correlation

FIG. 4

ROC curve: ROC of Ratio values in good/bad chondro

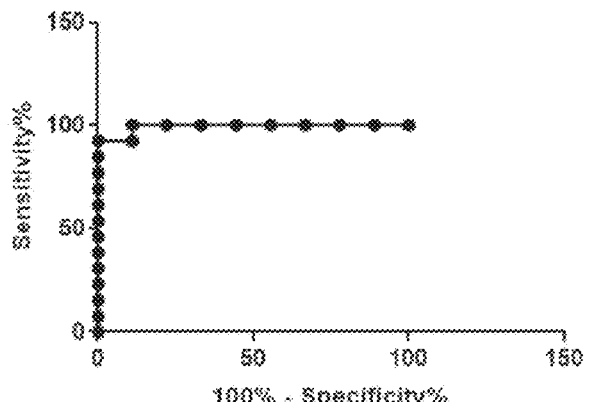

| Area under the ROC curve | |
|---|---|
| Area | 0.99145 |
| Std. Error | 0.013867 |
| 99% confidence interval | 0.95573 to 1.0000 |
| P value | 0.0061 |

FIG. 5

R1/R2 ratio values in "good" and "bad" chondrogenesis

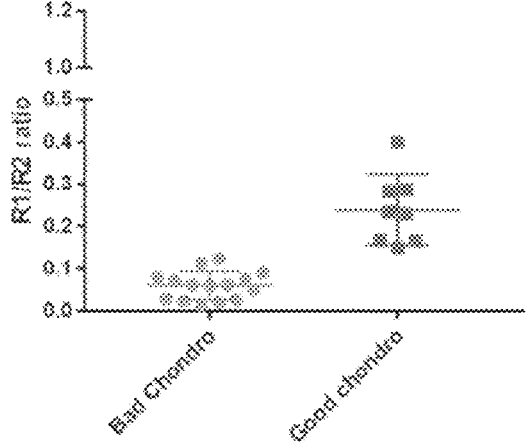

Samples were divided into.
Good - histological score 6-10
Bad - histological score 1-5
This division makes it possible to generate a
ROC curve and calculate cut-offs with different
associated specificity and sensitivity

FIG. 6

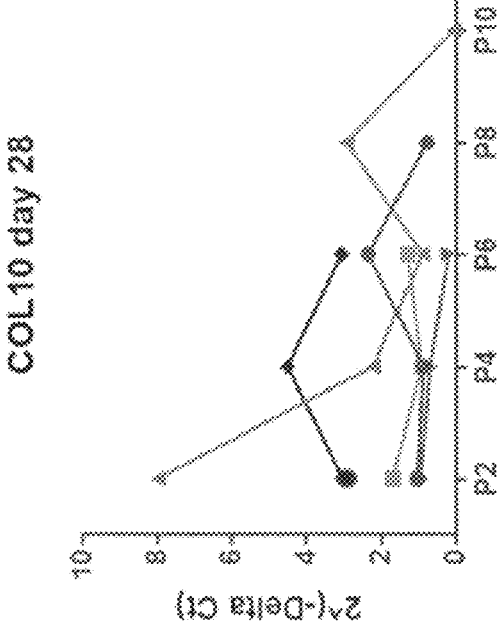
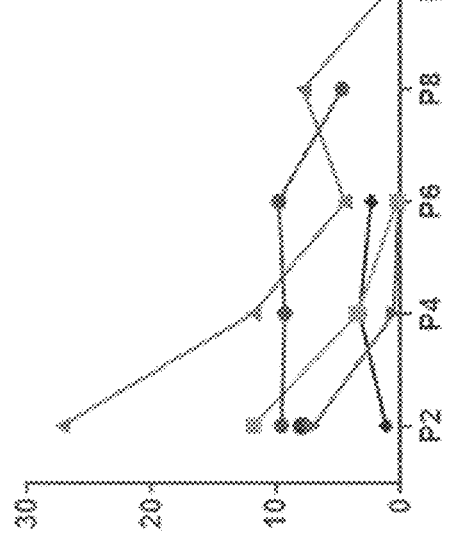
FIG. 7

A

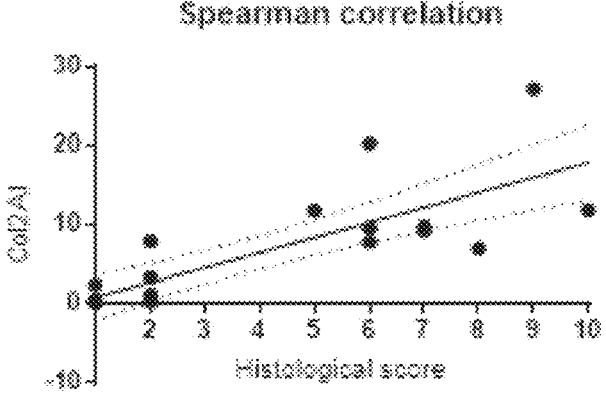

Spearman correlation

| Spearman r | |
|---|---|
| r | 0.8152 |
| 95% confidence interval | 0.5836 to 0.9245 |
| | |
| P value | |
| P (two-tailed) | 0.0001 |
| P value summary | *** |
| Exact or approximate P value | Approximate |
| Significant? (alpha = 0.05) | Yes |
| | |
| Number of XY Pairs | 21 |

Linear regression

| Slope | 1.196 to 2.591 |
|---|---|
| Y-intercept | -4.513 to 2.332 |

B

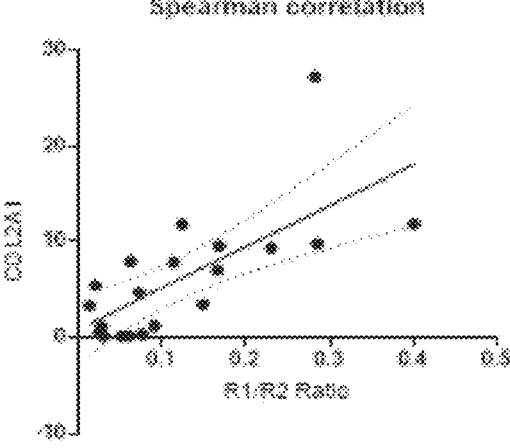

Spearman correlation

| Spearman r | |
|---|---|
| r | 0.7368 |
| 95% confidence interval | 0.4253 to 0.8923 |
| | |
| P value | |
| P (two-tailed) | 0.0002 |
| P value summary | *** |
| Exact or approximate P value | Approximate |
| Significant? (alpha = 0.05) | Yes |
| | |
| Number of XY Pairs | 20 |

Linear regression

| Slope | 21.48 to 64.19 |
|---|---|
| Y-intercept | -2.535 to 4.308 |

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<221> NAME/KEY: Artificial sequence
<222> LOCATION: 1..20
<223> OTHER INFORMATION: Synthetic oligonucleotide

<400> SEQUENCE: 1
tgggcaagaa caccatgatg                                              20

<210> SEQ ID NO 2
<211> LENGTH: 21
<212> TYPE: DNA
<213> ORGANISM: Artificial sequence
<220> FEATURE:
<221> NAME/KEY: Artificial sequence
<222> LOCATION: 1..21
<223> OTHER INFORMATION: Synthetic oligonucleotide

<400> SEQUENCE: 2
cggatatgag gcagcagttt c                                            21

<210> SEQ ID NO 3
<211> LENGTH: 24
<212> TYPE: DNA
<213> ORGANISM: Artificial sequence
<220> FEATURE:
<221> NAME/KEY: Artificial sequence
<222> LOCATION: 1..24
<223> OTHER INFORMATION: Synthetic oligonucleotide

<400> SEQUENCE: 3
agggcacctg gaaaacaacc cagc                                         24

<210> SEQ ID NO 4
<211> LENGTH: 22
<212> TYPE: DNA
<213> ORGANISM: Artificial sequence
<220> FEATURE:
<221> NAME/KEY: Artificial sequence
<222> LOCATION: 1..22
<223> OTHER INFORMATION: Synthetic oligonucleotide

<400> SEQUENCE: 4
ggcaatagca ggttcacgta ca                                           22

<210> SEQ ID NO 5
```

```
<211> LENGTH: 24
<212> TYPE: DNA
<213> ORGANISM: Artificial sequence
<220> FEATURE:
<221> NAME/KEY: Artificial sequence
<222> LOCATION: 1..24
<223> OTHER INFORMATION: Synthetic oligonucleotide

<400> SEQUENCE: 5
gataacagtc ttgccccact tacc                                                24

<210> SEQ ID NO 6
<211> LENGTH: 27
<212> TYPE: DNA
<213> ORGANISM: Artificial sequence
<220> FEATURE:
<221> NAME/KEY: Artificial sequence
<222> LOCATION: 1..27
<223> OTHER INFORMATION: Synthetic oligonucleotide

<400> SEQUENCE: 6
cctgaaggat ggctgcacga aacatac                                             27

<210> SEQ ID NO 7
<211> LENGTH: 20
<212> TYPE: DNA
<213> ORGANISM: Artificial sequence
<220> FEATURE:
<221> NAME/KEY: Artificial sequence
<222> LOCATION: 1..20
<223> OTHER INFORMATION: Synthetic oligonucleotide

<400> SEQUENCE: 7
acgctgaacg ataccaaatg                                                     20

<210> SEQ ID NO 8
<211> LENGTH: 27
<212> TYPE: DNA
<213> ORGANISM: Artificial sequence
<220> FEATURE:
<221> NAME/KEY: Artificial sequence
<222> LOCATION: 1..27
<223> OTHER INFORMATION: Synthetic oligonucleotide

<400> SEQUENCE: 8
tgctatacct ttactcttta tggtgta                                             27

<210> SEQ ID NO 9
<211> LENGTH: 33
<212> TYPE: DNA
<213> ORGANISM: Artificial sequence
<220> FEATURE:
<221> NAME/KEY: Artificial sequence
<222> LOCATION: 1..33
<223> OTHER INFORMATION: Synthetic oligonucleotide

<400> SEQUENCE: 9
actacccaac accaagacac agttcttcat tcc                                      33

<210> SEQ ID NO 10
<211> LENGTH: 20
<212> TYPE: DNA
<213> ORGANISM: Artificial sequence
<220> FEATURE:
<221> NAME/KEY: Artificial sequence
<222> LOCATION: 1..20
<223> OTHER INFORMATION: Synthetic oligonucleotide

<400> SEQUENCE: 10
```

-continued

```
cggccactcc ttaggtcttg                                                    20

<210> SEQ ID NO 11
<211> LENGTH: 24
<212> TYPE: DNA
<213> ORGANISM: Artificial sequence
<220> FEATURE:
<221> NAME/KEY: Artificial sequence
<222> LOCATION: 1..24
<223> OTHER INFORMATION: Synthetic oligonucleotide

<400> SEQUENCE: 11
ttttgccggt gtaggtgtag atag                                               24

<210> SEQ ID NO 12
<211> LENGTH: 26
<212> TYPE: DNA
<213> ORGANISM: Artificial sequence
<220> FEATURE:
<221> NAME/KEY: Artificial sequence
<222> LOCATION: 1..26
<223> OTHER INFORMATION: Synthetic oligonucleotide

<400> SEQUENCE: 12
ctccaaggac cctggagcac tcatgt                                             26
```

METHOD OF DETERMINING OR INFLUENCING THE CHONDROGENIC POTENTIAL OF MESENCHYMAL STROMAL CELLS

CROSS REFERENCE TO RELATED APPLICATIONS

This application is a National Stage of International Application No. PCT/EP2020/068848, filed Jul. 3, 2020, claiming priority to European Patent Application No. 19 184 241.8, filed Jul. 3, 2019.

INCORPORATION BY REFERENCE OF SEQUENCE LISTING

The content of the electronically submitted sequence listing, file name: Q271288SequenceListing.txt; size: 3,209 bytes; and date of creation: Dec. 12, 2025, is hereby incorporated by reference in their entirety.

TECHNICAL FIELD

The present invention relates to methods of increasing the chondrogenic potential mediated by TGFβ of a mesenchymal stromal cell or a population thereof, to methods of identifying a mesenchymal stromal cell (MSC) or a population of mesenchymal stromal cell (MSCs) exhibiting an increased chondrogenic potential mediated by TGFβ, and to methods of committing a mesenchymal stromal cell (MSC) to further differentiation in the chondrocytic lineage.

PRIOR ART

The use of human mesenchymal stromal cells (hMSCs) as source for cartilage, for both ex and in vitro use, is currently hampered by the inherent donor variation in terms of their ability to commit to further differentiation into chondrocytes, i.e. their chondrogenic potential.

Some donors may provide mesenchymal stromal cells that will exhibit a high chondrogenic potential while others may not. While already it is not satisfactory to be able to use only a subset of donors (the good donors) as a source for cartilage, the problem is further exacerbated by the fact that the identification of bad or good donors requires several rounds of donor cell culturing in chondrogenic medium and histological characterization.

In general, and in order to alleviate the problem of culturing of cell populations prior to using them for a certain purpose, a number of markers, such as CD marker profiles, have been proposed as markers enabling a prediction on the functional outcome of cell populations. However, at least in the case of mesenchymal stromal cells, CD marker profiles have been shown to be of little accuracy in determining the chondrogenic potential of mesenchymal stromal cell populations.

It would however be advantageous if the chondrogenic potential of mesenchymal stromal cells (hMSCs) could be easily determined prior to culturing, or use, and/or if the mesenchymal stromal cells (hMSCs) exhibiting a less than optimal chondrogenic potential could be stimulated into mesenchymal stromal cells (hMSCs) having an acceptable chondrogenic potential.

There exists thus a need for more accurately predicting the functional outcome, and in particular the chondrogenic potential, of cells or populations of cells such as mesenchymal stromal cells, to identify such cells or populations of cells and/or to restore the chondrogenic potential of cells or populations of cells lacking it.

SUMMARY OF THE INVENTION

The present invention thus provides for a method of increasing the chondrogenic potential of mesenchymal stromal cells, which chondrogenic potential is mediated by TGFβ, as well as a method of identifying mesenchymal stromal cells having an increased chondrogenic potential mediated by TGFβ, a method of committing a mesenchymal stromal cell (MSC) to further differentiation in the chondrocytic lineage, and chondrogenic implants comprising or void of mesenchymal stromal cells, inter alia.

The present invention is based on the finding that the ratio between the amount of the type I receptor TGFβR1 in a mesenchymal stromal cell and the amount of the type II receptor TGFβR2 in a mesenchymal stromal cell constitutes a reliable indicator of said mesenchymal cell's chondrogenic potential mediated by TGFβ, i.e. its ability to commit to further differentiation in the chondrocytic lineage under suitable conditions, i.e. when exposed to suitable levels of its ligand, TGFβ. Furthermore, the present invention is based on the finding that influencing said ratio between the amount of the type I receptor TGFβR1 in a mesenchymal stromal cell and the amount of the type II receptor TGFβR2 in a mesenchymal stromal cell will have an impact on said mesenchymal cell's chondrogenic potential mediated by TGFβ.

The present invention is further based on the finding that influencing the amount of another receptor of the TGFβ signaling pathway, ACVRL-I, can also influence the chondrogenic potential mediated by TGFβ in mesenchymal stromal cells.

The finding that the ratio between the amount of TGFβR1 in a mesenchymal stromal cell and the amount of TGFβR2 in a mesenchymal stromal constitutes an indicator of said mesenchymal cell's ability to commit to further differentiation in the chondrocytic lineage allows discriminating reliably between individual mesenchymal cells or populations thereof that can or cannot undergo efficiently further differentiation in the chondrocytic lineage, which is of importance in clinical application relating to the regeneration of cartilage or in research application where mesenchymal cells that reliably differentiate are an asset that allows to more efficiently conduct research and gather robust data. Furthermore, the finding that the ratio between the amount of TGFβR1 in a mesenchymal stromal cell and the amount of TGFβR2 in a mesenchymal stromal constitutes an indicator of said mesenchymal cell's ability to commit to further differentiation in the chondrocytic lineage opens the possibility to influence the mesenchymal stromal cell's fate towards the chondrocytic lineage or away from it by manipulating the amount of TGFβR1 and/or TGFβR2 in a mesenchymal stromal cell.

Analogously, the finding that another type I receptor of the TGFβ signaling pathway, ACVRL-I, can interact with the type II receptor TGFβR2 in the presence of TGFβ to decrease the chondrogenic potential mediated by TGFβ in mesenchymal stromal cells, opens the possibility to further control whether or not a mesenchymal stromal cell commits to further differentiation in the chondrocytic lineage in the presence of TGFβ by controlling the amount of ACVRL-I taken alone, or by concomitantly controlling the amounts of TGFβR1, TGFβR2 and ACVRL-I, or TGFβR1 and ACVRL-I or TGFβR2 and ACVRL-I.

It is consequently an object of the present invention to provide a method of increasing the chondrogenic potential mediated by TGFβ of a mesenchymal stromal cell (MSC), or a population of mesenchymal stromal cells (MSCs) comprising the step of increasing the amount of TGFβR1, and/or decreasing the amount of TGFβR2, and/or decreasing the amount of ACVRL-I of the MSC or the population of mesenchymal stromal cells (MSCs).

In the present invention, the mesenchymal stromal cells may be any mammalian mesenchymal stromal cells, and may be human mesenchymal stromal cells (hMSCs) such as for example human bone marrow derived mesenchymal stromal cells (hBMSCs). The mesenchymal cells may be isolated from tissues like bone marrow via established protocols which are readily available to the person skilled in the art.

It is understood that in the context of the present disclosure, an increase or decrease of the amount of a receptor such as TGFβR1, TGFβR2 or ACVRL-I can be brought about transiently or permanently and preferably is brought about transiently.

It is further understood that in the context of the present disclosure, the methods described therein may be carried out in vivo or ex vivo.

It is further an object of the present invention to provide a method of identifying a mesenchymal stromal cell (MSC) or a population of mesenchymal stromal cells (MSCs) exhibiting an increased chondrogenic potential mediated by TGFβ. Such a method is provided, in accordance with the present invention, comprising the steps of a. determining a first value reflective of the amount of TGFβR1 of said MSC or said population of MSCs, respectively;

b. determining a second value reflective of the amount of TGFβR2 of said MSC or said population of MSCs, respectively;

c. calculating the ratio between the first value and the second value;

d. determining if said ratio is 0.12 or higher, preferably 0.13 or higher, more preferably 0.135 or higher; and if so, e. identifying said MSC or population of MSCs as an MSC or population of MSCs, respectively, exhibiting an increased chondrogenic potential mediated by TGFβ.

It is understood that in the context of the present disclosure, and in particular in the context of a method of identifying a mesenchymal stromal cell (MSC) or a population of mesenchymal stromal cells (MSCs) exhibiting an increased chondrogenic potential mediated by TGFβ, the mesenchymal stromal cell (MSC) or a population of mesenchymal stromal cells (MSCs) may for example be comprised in a tissue sample or may be comprised in a culture of cells.

It is yet another object of the present invention to provide a method of committing a mesenchymal stromal cell (MSC) or a population of mesenchymal stromal cell (MSCs) to further differentiation in the chondrocytic lineage. Such a method is provided, in accordance with the present invention, comprising the steps of a. providing a mesenchymal stromal cell (MSC) or a population of mesenchymal stromal cells (MSCs), b. increasing the amount of TGFβR1 and/or decreasing the amount of TGFβR2 and/or decreasing the amount of ACVRL1 of the mesenchymal stromal cell (MSC) or of the population of mesenchymal stromal cells (MSCs), c. contacting the mesenchymal stromal cell (MSC) or the population of mesenchymal stromal cells (MSCs) having an increased amount of TGFβR1, and/or a decreased amount of TGFβR2 and/or a decreased amount of ACVRL1, with an effective amount of TGFβ, such as to commit said MSC to further differentiation in the chondrocytic lineage.

In the context of the present invention, the expression "effective amount of TGFβ" refers to an amount of TGFβ that allows a further differentiation of a MSC to occur. For example, an effective amount of TGFβ corresponds to a concentration of 1 ng/ml or more. Preferably, an effective amount of TGFβ corresponds to a concentration of 2, 3, 4, 5, 6, or up to 7 ng/ml or more, more preferably to a concentration of 8, 9 or 10 ng/ml or more.

It is additionally an object of the present invention to provide a chondrogenic implant comprising at least a scaffold for MSCs and a population of MSCs having an increased chondrogenic potential.

It is yet another object of the present invention to provide an essentially cell-free chondrogenic implant comprising a scaffold, wherein said scaffold comprises an agent capable of being released from the scaffold under physiological conditions and being capable of increasing the amount of TGFβR1 in MSCs and/or of decreasing the amount of TGFβR2 in MSCs and/or decreasing the amount of ACVRL1 in MSCs.

It is finally an object of the present invention to provide a use of the ratio between the amount of TGFβR1 of an MSC and the amount of TGFβR2 of an MSC or a population of MSCs for the identification of an MSC or a population of MSCs exhibiting an increased chondrogenic potential mediated by TGFβ.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIG. 1 shows the ratios between TGFβR1 and TGFβR2 as determined by RT-qPCR according to $R=2^{-(\Delta Ct_1 - \Delta Ct_2)}$ where $\Delta Ct_1 = Ct$ hTGFβ-RI–Ct hRPLP0 and $\Delta Ct_2 = Ct$ hTGFβ-RII–Ct hRPLP0 and with a house-keeping gene (in this case ribosomal protein large P0 (RPLP0)) as the reference gene and day 0 mRNA as the baseline; the figure shows the mean arbitrary unit ratios (AUR) between the amounts of TGFβR1 and TGFβR2 in hMSCs from 6 different donors (#120, #143, #168, #170, #195, #147,) at passages 2,4,6 and 8, as measured by RT-qPCR;

FIG. 2 shows representative Safranin-O stained pellets after chondrogenic induction of hMSCs of 5 different donors (#168, #120, #143, #168, #195, #170) with over multiple passages 2, 4, 6, 8 and 10.

FIG. 3 shows Safranin O stained pellets of a poor donor (CTR Positive) treated once with an siRNA to reduce receptor expression; knockdown of TGFβR2 and ACVRL1 lead to increased chondrogenesis; histological images (Collagen II [CIICI] upper row; Safranin-O lower row) revealing chondrogenic differentiation of hMSCs at day 21 in 3D micromass culture of donor #168 at passage 4 after electroporation with different siRNAs (negative, siTGFβR1, siTGFβR2 and siACVRL-1).

FIG. 4 shows the histological and molecular correlation of data from donors cohorts.

FIG. 5,6 show the data from donors cohorts divided by histological evaluation and receptor ratio FIG. 7 shows ROC curves for the determination of a cut-off value FIG. 8 shows the correlation of marker receptors ratio and Chondrogenic outcome markers FIG. 9 shows collagen II immunohistochemistry from pellets of a poor donor (CTR Positive) treated once with an siRNA to reduce receptor expression; knockdown of TGFβR2 and ACVRL1 lead to increased chondrogenesis.

DESCRIPTION OF PREFERRED EMBODIMENTS

In a preferred embodiment of the method of increasing the chondrogenic potential mediated by TGFβ of a mesenchymal stromal cell (MSC) or a population of mesenchymal stromal cells (MSCs) according to the present invention, the amount of TGFβR1 is increased by promoting the expression of TGFβR1, and/or the amount of TGFβR2 is decreased by, and/or the amount of ACVRL-I is decreased by at least partially inhibiting the expression of TGFβR2 of the mesenchymal stromal cell (MSC) or a population of mesenchymal stromal cells (MSCs).

It is understood that the increase in chondrogenic potential mediated by TGFb can be brought about in individual mesenchymal stromal cells (MSC) as well as in a plurality, or population, of mesenchymal cells such as for example MSC micropellets or cell cultures such as suspension cultures or adherent cultures.

It is understood by a person skilled in the art that the terms "mesenchymal stromal cell(s)" and "mesenchymal stem cell(s)" are used interchangeably in the art, and are herewith referred to as "mesenchymal stromal cell(s)" ("MSC(s)") without any limitation as to one or the other.

In a preferred embodiment of the method of increasing the chondrogenic potential mediated by TGFβ of a mesenchymal stromal cell (MSC) or a population of mesenchymal stromal cells (MSCs) according to the present invention, the amount of TGFβR1 of the MSC or of a population of mesenchymal stromal cells (MSCs) is increased and/or the amount of TGFβR2 of the MSC or the population of mesenchymal stromal cells (MSCs) is decreased such that the ratio between TGFβR1 and TGFβR2 of the MSC or the population of MSCs is 0.12 or higher, preferably 0.13 or higher, more preferably 0.135 or higher.

It is understood that the term "ratio between TGFβR1 and TGFβR2" may refer to either the ratio between the amounts TGFβR1 and TGFβR2 as directly determined in a MSC or a population of MSCs or alternatively may refer to the ratio between the amounts of TGFβR1 and TGFβR2 as indirectly determined in a MSC or a population of MSCs. For example, the amounts of TGFβR1 and TGFβR2 can be indirectly determined or estimated by measuring the relative expression levels of mRNA encoding the respective receptor in the MSC or a population of MSCs. For Example, relative expression levels of mRNA can be measured by fluorescence analysis, DNA chip analysis or via RT PCR in single cells or entire populations.

Alternatively, the amounts of TGFβR1 and TGFβR2 protein can be directly determined or estimated by measuring the levels of TGFβR1 and TGFβR2 by fluorescence analysis on the MSC or a population of MSCs. Analogously, amounts, increases or decreases in ACVRL-I can also be determined indirectly or directly as in the case of TGFβR1 and TGFβR2.

In a preferred embodiment of the method of increasing the chondrogenic potential mediated by TGFβ of a mesenchymal stromal cell (MSC) or a population of mesenchymal stromal cells (MSCs) according to the present invention, the ratio between TGFβR1 and TGFβR2 of the MSC or the population of MSCs is any ratio within the range of 0.12 to 0.6, preferably any ratio within the range of 0.13 to 0.5, more preferably any ratio within the range of 0.135 to 0.3.

In a preferred embodiment of the method of increasing the chondrogenic potential mediated by TGFβ of a mesenchymal stromal cell (MSC) or a population of mesenchymal stromal cells (MSCs) according to the present invention, the amount of ACVRL-I is decreased to about 50% or less, preferably to about 40%, 30%, 20% or less, most preferably to 10% or less of the initial amount of ACVRL-I.

In a preferred embodiment of the method of increasing the chondrogenic potential mediated by TGFβ of a mesenchymal stromal cell (MSC) or a population of mesenchymal stromal cells (MSCs) according to the present invention, the amount of ACVRL-I is decreased to essentially 0%. Stated alternatively, the gene encoding ACVRL-I may be essentially knocked-down or silenced, which may be preferably brought about by transient gene silencing mediated by appropriate siRNA. A suitable siRNA may for example be obtained from Ambion under the designation siACVRL-L.

In a preferred embodiment of the method of increasing the chondrogenic potential mediated by TGFβ of a mesenchymal stromal cell (MSC) or a population of mesenchymal stromal cells (MSCs) according to the present invention, the amount of TGFβR2 and/or the amount of ACVRL1 of a mesenchymal stromal cell (MSC) or a population of mesenchymal stromal cells (MSCs) is decreased by any suitable method known to the person skilled in the art, in particular by a method selected from the group consisting of gene knockdown of the expression of TGFβR2 and/or ACVRL1, a change of expression of a gene regulator of TGFβR2 and/or ACVRL1, growth factor treatment, RNA interference, siRNA and any other method capable of (preferably transiently) decreasing the amount of TGFβR2 and/or ACVRL1 of the MSC or the population of mesenchymal stromal cells (MSCs), and any combination thereof. In a more preferred embodiment of the method of increasing the chondrogenic potential mediated by TGFβ of a mesenchymal stromal cell (MSC) or a population of mesenchymal stromal cells (MSCs) according to the present invention, the amount of either TGFβR2, ACVRL1 or both is decreased by transient knockdown of the TGFβR2 and/or ACVRL1 gene, e.g. by transient gene silencing.

In the context of the present invention, the expression "transient" refers to a temporary change, for instance in gene expression, that does not modify the chromosomal DNA. A transient knockdown of a gene may for example be achieved by an oligonucleotide binding to an mRNA of interest or temporarily binding to a gene of interest. Oligonucleotides and techniques well known to the person skilled in the art are antisense oligonucleotides, siRNA and miRNA.

In a preferred embodiment of the method of increasing the chondrogenic potential mediated by TGFβ of a mesenchymal stromal cell (MSC) or a population of mesenchymal stromal cells (MSCs) according to the present invention, the amount of TGFβR1 of a mesenchymal stromal cell (MSC) or a population of mesenchymal stromal cells (MSCs) is increased by a method selected from the group consisting of overexpression of a gene, a change of expression of a gene regulator, gene transfer, gene knock-in, growth factor treatment and any other method increasing the amount of TGFβR1 of the MSC. In a much preferred embodiment of the method of increasing the chondrogenic potential mediated by TGFβ of a mesenchymal stromal cell (MSC) or a population of mesenchymal stromal cells (MSCs) according to the present invention, the amount of TGFβR1 is increased by transient overexpression of the TGFβR1 gene.

The above-mentioned methods for increasing or decreasing expression of a target gene are well-known to the person skilled in the art, and the choice and/or adaptation of such methods for the purpose of increasing or decreasing the amount of receptors of the present invention lie within the skill of the person skilled in the art.

In a preferred embodiment of the method of increasing the chondrogenic potential mediated by TGFβ of a mesenchymal stromal cell (MSC) or a population of mesenchymal stromal cells (MSCs) according to the present invention, said amount of TGFβR1, of TGFβR2, and of ACVRL1 of the MSC or the population of the MSCs refers to the amount of TGFβR1, of TGFβR2, and of ACVRL1 mRNA, respectively, or to the amount of TGFβR1, of TGFβR2, and of ACVRL1 protein, respectively. In a more preferred embodiment of the method of increasing the chondrogenic potential mediated by TGFβ of a mesenchymal stromal cell (MSC) or a population of mesenchymal stromal cells (MSCs) according to the present invention, the amount of TGFβR1, of TGFβR2, and of ACVRL1 of the MSC or the population of the MSCs refers to the amount of mRNA of TGFβR1, of TGFβR2, and of ACVRL1, respectively.

In a preferred embodiment of the method of increasing the chondrogenic potential mediated by TGFβ of a mesenchymal stromal cell (MSC) or a population of mesenchymal stromal cells (MSCs) according to the present invention, the ratio between TGFβR1 of the MSC and TGFβR2 of the MSC is a molar ratio.

In a preferred embodiment of the method of identifying a mesenchymal stromal cell (MSC) or a population of mesenchymal stromal cells (MSCs) exhibiting an increased chondrogenic potential mediated by TGFβ according to the present invention the ratio between the first value and the second value is any ratio within the range of 0.12 to 0.6, preferably within the range of 0.13 to 0.5, more preferably any ratio within the range of 0.135 to 0.3.

It has been recognized that when the ratio between the first value and the second value is any ratio above 0.12 or any ratio within the range of 0.12 to 0.6, the MSCs will reliably differentiate in the chondrocytic lineage when contacted with TGFβ, thereby providing a means to identify suitable mesenchymal stromal cells for the study of either the differentiation into chondrocytes as well as for their use in in vivo cartilage regeneration or ex vivo cartilage production.

In a preferred embodiment of the method of identifying a mesenchymal stromal cell (MSC) or a population of mesenchymal stromal cells (MSCs) exhibiting an increased chondrogenic potential mediated by TGFβ according to the present invention, the amount of TGFβR1, and of TGFβR2 of the MSC or the population of the MSCs refers to the amount of mRNA for TGFβR1 and of TGFβR2, respectively, or to the amount of protein TGFβR1 and of TGFβR2, respectively.

In a preferred embodiment of the method of identifying a mesenchymal stromal cell (MSC) or a population of mesenchymal stromal cells (MSCs) exhibiting an increased chondrogenic potential mediated by TGFβ according to the present invention, the potential of said population of MSCs refers to the aggregate or the average potential of said population, preferably the aggregate potential.

It is understood that the amount of receptors, in the context of the present invention and in the case of a plurality, or population, of mesenchymal stromal cells is taken, is determined for the totality of the mesenchymal cells. For instance, when the amount of receptors is determined via the corresponding mRNA, the mRNA is extracted after lysis of the population of mesenchymal cells, or preferably a sample of said population of MSCs, and pooled together. This means that any determination of the amount of receptors is carried out such that the amount determined corresponds to an aggregate amount of the individual cellular amounts. The thus obtained amounts may be compared directly, e.g. in the form of fluorescence intensity if determined via RT-qPCR, to determine the ration between them.

Real-time quantitative PCR (RT-qPCR) may for example be used to indirectly determine the amount of TGFβR1 and TGFβR2, and of the ratio between both in a mesenchymal stromal cell or a population thereof. It has been found that the amount of cDNA for TGFβR1 and/or TGFβR2 that can be detected in a mesenchymal stromal cell and the ratios between them can be correlated to the chondrogenic potential of the mesenchymal stromal cell or a population thereof. For example, suitable primers for use in the determination of the amount of TGFβR1 and TGFβR2, and of the ratio between both using RT-qPCR may be designed using known primer design software or are readily available for purchase. As an example, primers suitable for use in the present invention are listed in Table 1.

In a preferred embodiment of the method of identifying a mesenchymal stromal cell (MSC) or a population of mesenchymal stromal cells (MSCs) exhibiting an increased chondrogenic potential mediated by TGFβ according to the present invention, the ratio between TGFβR1 and TGFβR2 is determined by RT-qPCR according to $R=2^{-(\Delta Ct_1 - \Delta Ct_2)}$, where $\Delta Ct_1 = $ Ct hTGFβ-RI–Ct (housekeeping gene) and $\Delta Ct_2 = $ Ct hTGFβ-RII–Ct (housekeeping gene) and with the housekeeping gene as the reference gene and preferably day 0 mRNA as the baseline. As housekeeping gene reference, any suitable housekeeping gene may be used that is known to the person skilled in the art, e.g. ribosomal protein large P0 (RPLP0).

In a preferred embodiment of the method of committing a mesenchymal stromal cell (MSC) or a population of mesenchymal stromal cell (MSCs) to further differentiation in the chondrocytic lineage according to the present invention, the amount of TGFβR2 and/or the amount of ACVRL1 of the MSC or the population of MSCs is decreased by a method selected from the group consisting of gene knockdown of the expression of TGFβR2 and/or ACVRL1, a, change of expression of a gene regulator of TGFβR2 and/or ACVRL1, growth factor treatment, RNA interference, and any other method decreasing the amount of TGFβR2 and/or ACVRL1 of the MSC, and any combination thereof, preferably by transient gene knockdown of the TGFβR2 and/or ACVRL1 gene.

In a preferred embodiment of the method of committing a mesenchymal stromal cell (MSC) or a population of mesenchymal stromal cell (MSCs) to further differentiation in the chondrocytic lineage according to the present invention, the amount of TGFβR1 of the mesenchymal stromal cell (MSC) or a population of mesenchymal stromal cells (MSCs) is increased by a method selected from the group consisting of overexpression of a gene, a change of expression of a gene regulator, gene transfer, growth factor treatment and any other method increasing the amount of TGFβR1 of the MSC, preferably by a transient overexpression of the TGFβR1 gene.

In a preferred embodiment of the method of committing a mesenchymal stromal cell (MSC) or a population of mesenchymal stromal cell (MSCs) to further differentiation in the chondrocytic lineage according to the present invention, the amount of TGFβR1 of the MSC or of the population of MSCs is increased and/or the amount of TGFβR2 of the MSC or the population of MSCs is decreased such that the ratio between TGFβR1 and TGFβR2 of the MSC or the population of MSCs is 0.12 or higher, preferably 0.13 or higher, more preferably 0.135 or higher.

In a preferred embodiment of the method of committing a mesenchymal stromal cell (MSC) or a population of mesenchymal stromal cell (MSCs) to further differentiation in the chondrocytic lineage according to the present invention, the ratio between TGFβR1 and TGFβR2 of the MSC or the population of MSCs is any ratio within the range of 0.12 to 0.6, preferably any ratio within the range of 0.13 to 0.5, more preferably any ratio within the range of 0.135 to 0.3.

In a preferred embodiment of the method of committing a mesenchymal stromal cell (MSC) or a population of mesenchymal stromal cell (MSCs) to further differentiation in the chondrocytic lineage according to the present invention, the amount of ACVRL-I is decreased to about –50% or less, preferably to about 40%, 30%, 20% or less, most preferably to 10% or less of the initial amount of ACVRL-in the MSC or populations of MSCs.

In a preferred embodiment of the method of committing a mesenchymal stromal cell (MSC) or a population of mesenchymal stromal cell (MSCs) to further differentiation in the chondrocytic lineage according to the present invention, the amount of ACVRL1 is decreased to essentially 0% of its expression level.

In a preferred embodiment of the method of committing a mesenchymal stromal cell (MSC) or a population of mesenchymal stromal cell (MSCs) to further differentiation in the chondrocytic lineage according to the present invention, the amount of TGFβR1, of TGFβR2, and of ACVRL1 of the MSC or the population of the MSCs refers to the amount of mRNA of TGFβR1, of TGFβR2, and of ACVRL1, respectively, or to the amount of protein TGFβR1, of TGFβR2, and of ACVRL1 protein, respectively.

In a preferred embodiment of the method of committing a mesenchymal stromal cell (MSC) or a population of mesenchymal stromal cell (MSCs) to further differentiation in the chondrocytic lineage according to the present invention, the ratio between TGFβR1 and TGFβR2 of the MSC or the population of the MSCs is a molar ratio.

In another embodiment, the present invention provides a chondrogenic implant comprising at least a scaffold for MSCs and a population of MSCs having an increased chondrogenic potential.

In a preferred embodiment of the chondrogenic implant according to the present invention, the population of MSCs, preferably before including it in the chondrogenic implant, a. has been subjected to a method in accordance with any of claims 1 to 10; or b. has been subjected to a method in accordance with any of claims 15 to 22; or c. has been identified to have an increased chondrogenic potential by a method in accordance with any of claims 11 to 14.

In a preferred embodiment of the chondrogenic implant according to the present invention, at least a fraction of individual MSCs within said population of MSCs exhibits an increased chondrogenic potential.

In a preferred embodiment of the chondrogenic implant according to the present invention, the fraction of individual MSCs within said population is larger than 25%, preferably larger than 30%, 40%, 50%, 60%, 70% or even 80%, 90%, 95% or more.

In a preferred embodiment of the chondrogenic implant according to the present invention, the MSCs exhibiting an increased chondrogenic potential within said population of MSCs are characterized in that the amount of TGFβR1 of the MSC is increased, and/or the amount of TGFβR2 and/or ACVRL1 of the MSC is decreased.

In a preferred embodiment of the chondrogenic implant according to the present invention, the amount of TGFβR1 of the MSC or of the population of MSCs is increased and/or the amount of TGFβR2 of the MSC or the population of MSCs is decreased such that the ratio between TGFβR1 and TGFβR2 of the MSC or the population of MSCs is 0.12 or higher, preferably 0.13 or higher, more preferably 0.135 or higher.

In a preferred embodiment of the chondrogenic implant according to the present invention, the ratio between TGFβR1 and TGFβR2 of the MSC or the population of MSCs is any ratio within the range of 0.12 to 0.6, preferably any ratio within the range of 0.13 to 0.5, more preferably any ratio within the range of 0.135 to 0.3.

In a preferred embodiment of the chondrogenic implant according to the present invention, the amount of ACVRL1 is decreased to about 50% or less, preferably to about 40%, 30%, 20% or less, most preferably to 10% or less of the initial amount of ACVRL-in the MSC or populations of MSCs.

In a preferred embodiment of the chondrogenic implant according to the present invention, the amount of ACVRL1 is decreased to essentially 0% of its expression level.

In another embodiment of the present invention, an essentially cell-free chondrogenic implant is provided. In accordance with the present invention, the essentially cell-free chondrogenic implant comprises at least a scaffold suitable to carry an agent capable of being released from the scaffold after implantation under physiological conditions, wherein the agent is capable of increasing the amount of TGFβR1 in MSCs and/or of decreasing the amount of TGFβR2 in MSCs and/or decreasing the amount of ACVRL1 in MSCs.

In a preferred embodiment of the essentially cell-free chondrogenic implant according to the present invention, the agent increasing the amount of TGFβR1 is selected from the group consisting of small molecules, DNA vectors, RNA vectors, siRNA, RNAi, microRNA or proteins such as for example growth factors.

In another preferred embodiment of the essentially cell-free chondrogenic implant according to chondrogenic implant according to the present invention, the agent decreasing the amount of TGFβR2 or the agent decreasing the amount of ACVRL1 is selected from the group consisting of small molecules, DNA vectors, RNA vectors, siRNA, RNAi, microRNA or proteins such as for example growth factors.

EXAMPLES

Material and Methods

Human Mesenchymal Stromal cell isolation from fresh Bone Marrow Bone marrow from different donors was harvested from vertebral body after informed consent (Ethical approval: Freiburg, EK-326/08). Fresh bone marrow was diluted 1:4 and layered on top of Ficoll, in a proportion of 2.6 ml of Ficoll per ml of undiluted marrow. After centrifugation at 500 g for 20 minutes, the mononuclear cell-containing interface was recovered, and cells were counted using the Cell Scepter 2.0 Automated Cell Counter (Millipore). Isolated cells were seeded at a density of 50,000 cells/cm$^2$ into 300 cm$^2$ tissue culture flasks in Minimum Essential Medium Eagle, Alpha Modification ($\alpha$-MEM; Gibco) containing 10% fetal bovine serum (Sera Plus, PAN-Biotec cat number: lot number:), 100 U/mL penicillin, and 100 µg/mL streptomycin (Gibco), and 5 ng/ml recombinant human basic fibroblast growth factor (bFGF). Cells were maintained at 37° C. in 5% $CO_2$, 85% humidity atmosphere. Medium was refreshed every 2$^{nd}$ day. After 4 days, non-adherent hematopoietic cells were removed to select the mesenchymal stromal cell (hMSC) population.

Passaging hMSCs were cultured from passage 0 to passage 10, with an initial seeding density of 3000 cells/cm$^2$ in 300 cm$^2$ tissue culture flasks, in the conditions described above. When reaching 80% confluency, images of cells were taken in order to record their morphology. Cultures were then passaged and RNA isolated for the evaluation of the TGFβ-Receptor expression.

Chondrogenic Differentiation

Differentiation along the chondrogenic lineage of the hMSCs was performed in 3D micromass culture. A quantity of 2×10$^5$ hMSCs per micromass were seeded in V-bottom 96-well plates (Costar #3894). To prevent possible cell adhesion on the bottom, the plate was pre-coated with 20 µl of 1% agarose. Cells were centrifuged for 5 minutes at 500 g in order to form the pellets for micromass organization. Chondrogenic differentiation medium contained DMEM High Glucose (Gibco), 1% Non essential Amino Acids (ThermoFisher), 1% ITS+(Corning), 100 nM Dexamethasone (Fitzgerald), 10 ng/ml TGF-β1 (Fitzgerald) and 50 µg/ml Ascorbic acid-2 phosphate. The control growth medium contained DMEM high Glucose (Gibco), 1% Non essential Amino Acids (ThermoFisher), 1% ITS+(Corning). The medium was replaced every second day and pellets were harvested for further analyses at 7,14 and 21 days.

Transfection and Receptor Silencing

In order to demonstrate the role of TGFβ receptors during chondrogenic commitment and their relevance during TGFβ signaling pathway activation, TGFβ-RI, TGFβ-RII, and ACVRL-I were transiently inhibited. According to manufactures' protocol of NEON transfection system, hMSC were resuspended in Buffer R at a final concentration of 0.5×10$^7$ cells/ml. Cells were transfected with either siTGFβ-RI (Ambion), siTGFβ-RII (Ambion), siACVRL-I (Ambion) at 25 nM, or scramble control (siNegative) by electroporation using a 990 Pulse Voltage, 40 ms Pulse width for 1 Pulse number using 100 µl tip. Cells were then transferred in chondrogenic medium or control medium in absence of antibiotics.

Real-Time Quantitative PCR Analysis

Total RNA was isolated from adherent hMSCs after trypsinisation during passaging and from 3D chondrogenic induced micromass at day 0, 7, 14 and 28 using TRI Reagent® Solution (Molecular Research Center MRC, cat. #TR-118) according to the manufacturer's protocol. RNA quantity was measured using a NanoDrop 1000 Spectrophotometer (Thermo Fisher). For reverse transcription, TaqMan Reverse Transcription Kit (Applied Biosystems, Foster City, USA) was used. The RT reaction was carried out at 25° C. for 10 min, followed by 1 h at 42° C. and stopped by heating for 5 min at 85° C. qPCR reactions were set up in 10 µL reaction mixtures containing TaqMan Universal Master Mix (Thermo Fischer), Primer and Probe (hRPLP0) or Assay-OnDemand, DEPC-$H_2O$ and cDNA template. The reaction program was set up as follows: 50° C. for 2 minutes, 95° C. for 10 minutes and 40 cycles of 95° C. for 15 seconds followed by an annealing/extension step at 60° C. for 1 minute. qPCR analysis was performed using QuantStudio 6 and 7 Flex Real-Time PCR System (Life Technologies, Carlsbad, USA). Duplicates were used for each target gene (technical replicates) and triplicates for each donor (biological replicates).

The relative expression of RUNX2, SOX9, ACAN, MMP13, COL2A1, COL10A1 during chondrogenic differentiation was determined using the $2^{(-\Delta\Delta Ct)}$ method, with ribosomal protein large, P0 (RPLP0) as reference gene and day 0 RNA as the baseline, where $\Delta\Delta C_t$ is $\Delta Ct_1 - \Delta Ct_2$.

The ratio between of TGFβR1 and of TGFβR2 expression was determined using $\Delta Ct$ values $R = 2^{-(\Delta Ct_1 - \Delta Ct_2)}$ Where $\Delta Ct_1 =$ Ct hTGFβ-RI–Ct hRPLP0 and $\Delta Ct_2 =$ Ct hTGFβ-RII–Ct hRPLP0

Primer and probe sequences as well as Order Numbers of Assays-on-Demand (Applied Biosystems) are listed in Table 1.

TABLE 1

| Name of Gene | Name of Primer/Sequence | Type | Producer |
|---|---|---|---|
| hACVRL-I | Hs01050825_s1 | On Demand | Applied Biosystem |
| hACVR1 | Hs00153836_m1 | On Demand | Applied Biosystem |
| hACVR1B | Hs00244715_m1 | On Demand | Applied Biosystem |
| hACVR1C | Hs00899854_m1 | On Demand | Applied Biosystem |
| hACVR2A | Hs00155658_m1 | On Demand | Applied Biosystem |
| hACVR2B | Hs00609603_m1 | On Demand | Applied Biosystem |
| hBMP-R1A | Hs01034913_g1 | On Demand | Applied Biosystem |

TABLE 1-continued

| Name of Gene | Name of Primer/Sequence | Type | Producer |
|---|---|---|---|
| hBMP-R1B | Hs01010965_m1 | On Demand | Applied Biosystem |
| hBMP-R2 | Hs00176148_m1 | On Demand | Applied Biosystem |
| hTGFβ-RI | Hs00610320_m1 | On Demand | Applied Biosystem |
| hTGFβ-RII | Hs00234253_m1 | On Demand | Applied Biosystem |
| hSOX9 | Hs00165814_m1 | On Demand | Applied Biosystem |
| hACAN | Hs01050178_m1 | On Demand | Applied Biosystem |
| hRPLP0 fwd | 5'-TGG GCA AGA ACA CCA TGA TG-3' | Primer & Probe | MicroSynth |
| hRPLP0 rev | 5'-CGG ATA TGA GGC AGC AGT TTC-3' | Primer & Probe | MicroSynth |
| hRPLP0 Pr | 5'-AGG GCA CCT GGA AAA CAA CCC AGC-3' | Primer & Probe | MicroSynth |
| hCol2A1 fwd | 5'-GGC AAT AGC AGG TTC ACG TAC A-3' | Primer & Probe | MicroSynth |
| hCol2A1 rev | 5'-GAT AAC AGT CTT GCC CCA CTT ACC-3' | Primer & Probe | MicroSynth |
| hCol2A1 Pr | 5'-CCT GAA GGA TGG CTG CAC GAA ACA TAC-3' | Primer & Probe | MicroSynth |
| hCol10A1 fwd | 5'-ACG CTG AAC GAT ACC AAA TG-3' | Primer & Probe | MicroSynth |
| hCol10A1 rev | 5'-TGC TAT ACC TTT ACT CTT TAT GGT GTA-3' | Primer & Probe | MicroSynth |
| hCol10A1 Pr | 5'-ACT ACC AAA CAC CAA GAC ACA GTT CTT CAT TCC-3' | Primer & Probe | MicroSynth |
| hMMP13 fwd | 5'-CGG CCA CTC CTT AGG TCT TG-3' | Primer & Probe | MicroSynth |
| hMMP13 rev | 5'-TTT TGC CGG TGT AGG TGT AGA TAG-3' | Primer & Probe | MicroSynth |
| hMMP13 Pr | 5'-CTC AAA GGA CCC TGG AGC ACT CAT GT-3' | Primer & Probe | MicroSynth |

Histological Staining

At day 28, samples were fixed in 70% methanol. Cryosections were cut with a thickness of 8-10 μm. For Safranin-O-Staining, samples were first stained with Weigert's Haematoxylin for 10 minutes, followed by a six minute stain with Fast Green and a 15 minutes stain with Safranin-O. After dehydration with increasing concentrations of ethanol, samples were coverslipped with the use of xylene.

For collagen II staining a monoclonal antibody (CIICI, DSHB, Iowa, USA) was used. After incubating slides in methanol for 30 minutes, nonspecific binding sites were blocked with horse serum (Vector Laboratories #S-2000; Dilution 1:20) for one hour. Primary antibody was then added for 30 minutes (Dilution 1:6) followed by an incubation in Biotinylated Anti-Mouse IgG (H+L) secondary antibody (Vector Laboratories #BA-2001; Dilution 1:200) and a second incubation in Vectastain Elite ABC Kit (Vector Laboratories #PK-6100). ImmPACT DAB solution (Vector Laboratories #SK-4105) was added as substrate for peroxidase for 4 minutes. Counterstaining was performed using Mayer's Haematoxylin (Fluka #51275) for 20 seconds. After dehydration with increasing concentrations of ethanol, samples were coverslipped with the use of xylene.

RESULTS AND CONCLUSIONS

To allow prediction of the chondrogenic potential of a cell population without the need to refer to a normalizer/calibrator, RT-qPCR was carried out on hMSC samples from different donors and the ratio R between TGFβR1 and TGFβR2 was quantified using the equation $R=2^{-(\Delta ct_1 - \Delta Ct_2)}$, as disclosed above. This allows for the population of cells to be assessed in isolation. The ratio was evaluated directly after cell harvest from tissue culture plastic. There was a trend towards a general decrease in ratio during in vitro aging, i.e. the number of passaging (P #). However, the rate of change varied depending on the donor. The ratio at the time of cell harvest correlated with the chondrogenic potential as assessed by safranin O staining and immunohistochemistry from collagen II.

The quality of chondrogenic differentiation strongly varied among the donors, some donors were considered good (170) and maintained a high yield of differentiation over the time, whereas other donors (168) were considered bad already in the early phase and showed a poor chondrogenesis, see FIG. 1. Because histological evaluation usually takes place after 21/28 days, it is necessary to find a way that can be predictive and representative before inducing the differentiation for all cells not only in high passage. Donor 168, from early passages, showed a low ratio R with a dramatic decrease between p4 and p5; alternatively, donor 170 showed a high ratio R since passage p2 that remained almost constant even over passage 4. Those molecular analyses were later confirmed on the histological level in chondrogenic differentiation shown by Saf-O-staining at 28 days, see FIG. 2.

In accordance with the histological evaluation seen in FIG. 2, all the ratios with a ratio R in excess of about 0.12 were associated to a cell population with a high yield and a good quality of differentiation. The ratio trend, as expected, changed over time, i.e. decreased over the passaging according with the lower expression of TGFβ-RI and subsequent increase of TGFβ-RII, probably due to the aged cells status. Occasionally the ratio increased and this was reflected in an increase in chondrogenic potential.

The use of the ratio R allows the prediction of hMSC chondrogenic outcome prior to the induction of differentiation. For the donors not showing any chondrogenic potential, i.e. a ratio R below 0.12, it was possible to alter the fate of their hMSCs by transiently knocking down TGFβ-R2 using a single dose of siRNA to shift the ratio R back to a value in excess of 0.12.

Figure 3:
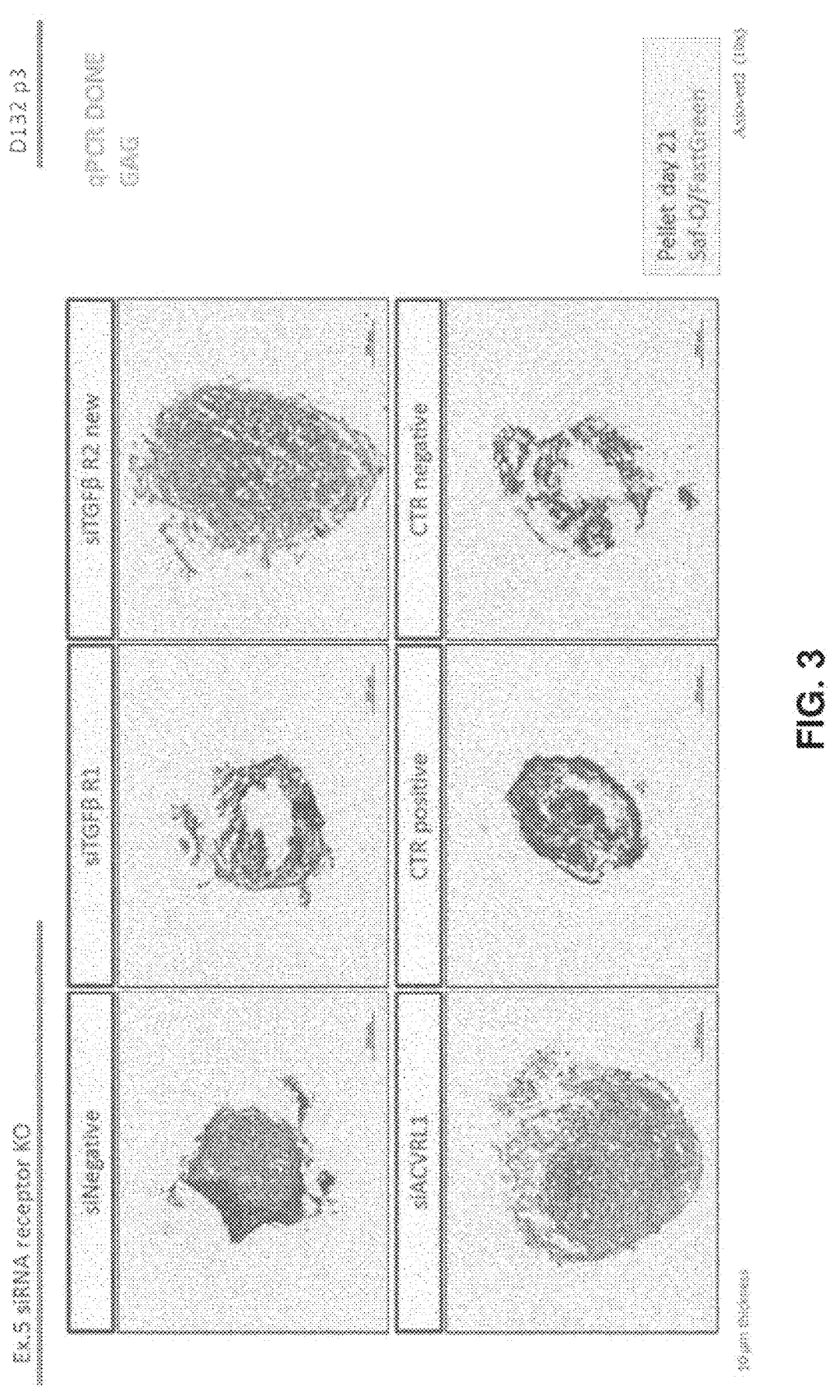

For those donors that showed ratio R of more than 0.12, no changes during differentiation upon silencing of TGFβ-R2 was observed. All donors with a ratio R below 0.12 positively responded to the silencing of TGFβ-R2 with a marked enhancement of matrix deposition that was clearly demonstrated by Saf-O staining. Likewise, transiently knocking down ACVRL1 also increased a marked enhancement of matrix deposition that was clearly demonstrated by Saf-O staining, see FIG. 3.

To identify the cut-off value below which the population no longer is chondrogenic, a further 22 samples were analyzed, and the ratio R was correlated to histological outcomes ranked on a scale of 1-10 as assessed by four blinded evaluators, see FIG. 4. Based on this, samples were then separated based on histological evaluation of four different operators and samples with histological scores between 1 and 5 were considered BAD, i.e. non chondrogenic, samples with histological score between 6 and 10 were considered GOOD, i.e. chondrogenic, see FIG. 6. In FIG. 6, the two cohorts based on GOOD and BAD for the respective TGFB ratio were further evaluated to determine a precise cutoff number generated by ROC analysis, see also FIG. 5. A value of 0.136 was established as the cut-off value for determining if an hMSC was chondrogenic (above 0.136) or not (below 0.136), according to the below data.

| | Sensitivity % | 99% CI | Specificity % | 99% CI | Likelihood ratio |
|---|---|---|---|---|---|
| <0.016762 | 7.6923 | 0.038551% to | 100.00 | 55.505% to | |
| <0.022103 | 15.385 | 0.82522% to | 100.00 | 55.505% to | |
| <0.025745 | 23.077 | 2.7832% to | 100.00 | 55.505% to | |
| <0.028598 | 30.769 | 5.7076% to | 100.00 | 55.505% to | |
| <0.040037 | 38.462 | 9.4229% to | 100.00 | 55.505% to | |
| <0.055542 | 46.154 | 13.827% to | 100.00 | 55.505% to | |
| <0.061292 | 53.846 | 18.870% to | 100.00 | 55.505% to | |
| <0.066918 | 61.538 | 24.543% to | 100.00 | 55.505% to | |
| <0.074321 | 69.231 | 30.872% to | 100.00 | 55.505% to | |
| <0.078305 | 76.923 | 37.936% to | 100.00 | 55.505% to | |
| <0.085587 | 84.615 | 45.896% to | 100.00 | 55.505% to | |
| <0.10252 | 92.308 | 55.098% to | 100.00 | 55.505% to | |
| <0.11893 | 92.308 | 55.098% to | 88.889 | 41.503% to | 8.3077 |
| <0.13652 | 100.00 | 66.527% to | 88.889 | 41.503% to | 9.0000 |
| <0.15781 | 100.00 | 66.527% to | 77.778 | 30.739% to | 4.5000 |
| <0.16745 | 100.00 | 66.527% to | 66.667 | 21.914% to | 3.0000 |
| <0.19909 | 100.00 | 66.527% to | 55.556 | 14.606% to | 2.2500 |
| <0.23206 | 100.00 | 66.527% to | 44.444 | 8.6788% to | 1.8000 |
| <0.25850 | 100.00 | 66.527% to | 33.333 | 4.1585% to | 1.5000 |
| <0.28397 | 100.00 | 66.527% to | 22.222 | 1.2124% to | 1.2857 |
| <0.34286 | 100.00 | 66.527% to | 11.111 | 0.055679% to | 1.1250 |

Recovery of Chondrogenic Phenotype

Figure 9:
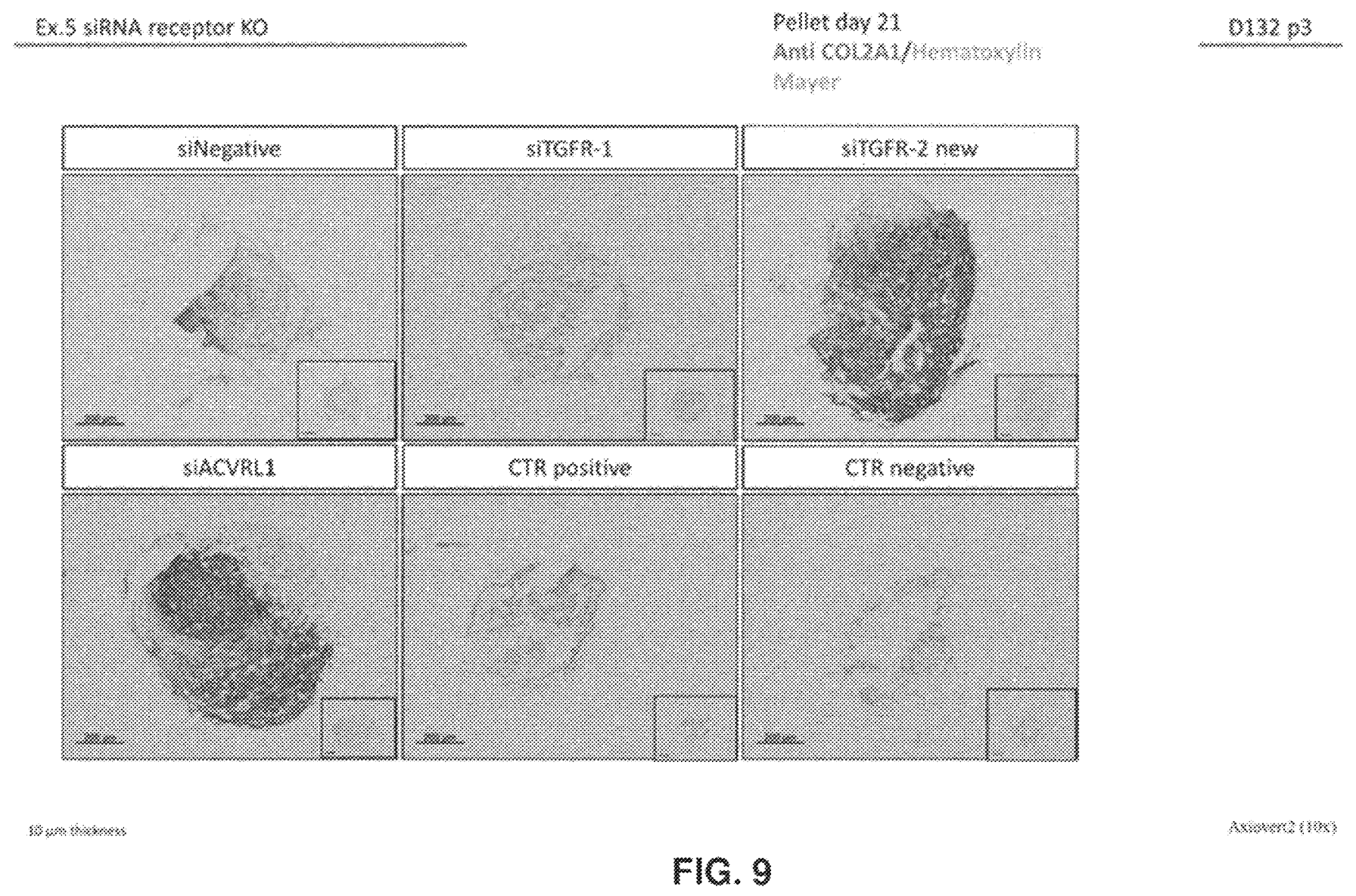

The ratio R allows the prediction of hMSC chondrogenic outcome prior to the induction of differentiation in chondrogenic medium. Of the donors investigated, the donors that did not show any chondrogenic potential could be predicted by the receptor ratio on the day of cell harvest as not having a chondrogenic potential. However, in order to confirm the causal role of the receptor profile in association to the fate of hMSCs, the various receptors were transiently knocked-down using a single dose of siRNA and analysed histologically, see FIG. 9.

For those donors that showed a high ratio R, no changes during differentiation upon silencing of TGFβ-Rs was observed (data not shown). On the contrary, all donors with low ratio R positively responded to the silencing of TGFβ-

RII, with a marked enhancement of matrix deposition that was clearly demonstrated by Saf-O staining and COL2A1 protein expression revealed by immunohistochemistry, see also FIGS. 3 and 10. This evidence confirms observations on TGFβ-Rs ratio and demonstrates that it is possible to interfere with a "predetermined" fate associated with the TGFβ-Rs profile and revert it. It also confirms that a high expression of TGFβ-RII can be a possible reason of poor chondrogenic differentiation, not only in aged cells during passaging, but also in early stages. Interestingly, while the silencing of TGFβ-RI did not significantly alter differentiation in comparison to the negative scramble control, ACVRL-I knockdown also led to increased chondrogenic potential, see FIGS. 3 and 9.

---

The invention claimed is:

1. A method of increasing the chondrogenic potential mediated by Transforming Growth Factor Beta Receptors (TGFβR) of a mesenchymal stromal cell (MSC) or a population of mesenchymal stromal cells (MSCs), comprising the steps of:

increasing the amount of Transforming Growth Factor Beta Receptor 1 (TGFβR1), and decreasing the amount of Transforming Growth Factor Beta Receptor 2 (TGFβR2), wherein the amount of TGFβR1 is increased by promoting the expression of TGFβR1, and the amount of TGFβR2 is decreased by at least partially inhibiting the expression of TGFβR2, wherein the amount of TGFβR1 of the MSC or the population of MSCs is increased and the amount of TGFβR2 of the MSC or the population of MSCs is decreased such that the ratio between TGFβR1 and TGFβR2 of the MSC or the population of MSCs is within the range of 0.12 to 0.6.

2. The method according to claim 1, wherein additionally, the amount of Activin A receptor, type II-like 1 (ACVRL1) is decreased to about 50% or less of the initial amount of ACVRL1 in the MSC or populations of MSCs.

3. The method according to claim 1, wherein the amount of ACVRL1 is decreased to essentially 0% of its expression level.

4. The method according to claim 1, wherein the amount of TGFβR2 and/or the amount of ACVRL1 of the MSC or the population of MSCs is decreased by a method selected from the group consisting of gene knockdown of the expression of TGFβR2 and/or ACVRL1, a change of expression of a gene regulator of TGFβR2 and/or ACVRL1, growth factor treatment, RNA interference, and any other method decreasing the amount of TGFβR2 and/or ACVRL1 of the MSC, and any combination thereof, and/or wherein the amount of TGFβR1 of the mesenchymal stromal cell (MSC) or a population of mesenchymal stromal cells (MSCs) is increased by a method selected from the group consisting of overexpression of a gene, a change of expression of a gene regulator, gene transfer, growth factor treatment and any other method increasing the amount of TGFβR1 of the MSC.

5. The method according to claim 1, wherein said amount of TGFβR1, of TGFβR2, and of ACVRL1 of the MSC or the population of the MSCs refers to the amount of mRNA of TGFβR1, of TGFβR2, and of ACVRL1, respectively, or to the amount of protein TGFβR1, of TGFβR2, and of ACVRL1 protein, respectively.

6. The method according to claim 1, wherein said ratio between TGFβR1 of the MSC and TGFβR2 of the MSC is a molar ratio.

7. A method of identifying a mesenchymal stromal cell (MSC) or a population of mesenchymal stromal cells (MSCs) exhibiting an increased chondrogenic potential mediated by Transforming Growth Factor Beta Receptors (TGFβR), comprising the steps of a. determining a first value reflective of the amount of Transforming Growth Factor Beta Receptor 1 (TGFβR1) of said MSC or said population of MSCs, respectively;

b. determining a second value reflective of the amount of Transforming Growth Factor Beta Receptor 2 (TGFβR2), of the MSC or population of MSCs, respectively;

c. calculating the ratio between the first value and the second value;

d. determining if said ratio is within the range of 0.12 to 0.6; and if so, e. identifying said MSC or population of MSCs as an MSC or population of MSCs, respectively, exhibiting an increased chondrogenic potential mediated by TGFβ.

8. The method according to claim 7, wherein said amount of TGFβR1, and of TGFβR2 of the MSC or the population of the MSCs refers to the amount of mRNA of TGFβR1 and of TGFβR2, respectively, or to the amount of protein TGFβR1, of TGFβR2, respectively.

9. The method according to claim 7, wherein the potential of said population of MSCs refers to the aggregate or the average potential of said population.

10. A method of committing a mesenchymal stromal cell (MSC) or a population of mesenchymal stromal cell (MSCs) to further differentiation in the chondrocytic lineage, comprising the steps of a. providing a mesenchymal stromal cell (MSC) or a population of mesenchymal stromal cells (MSCs), b. increasing the amount of Transforming Growth Factor Beta Receptor 1 (TGFβR1) and decreasing the amount of Transforming Growth Factor Beta Receptor 2 (TGFβR2) of the mesenchymal stromal cell (MSC) or of the population of mesenchymal stromal cells (MSCs) such that the ratio between TGFβR1 and TGFβR2 of the MSC or the population of MSCs is within the range of 0.12 to 0.6, c. contacting the mesenchymal stromal cell (MSC) or the population of mesenchymal stromal cells (MSCs) having an increased amount of TGFβR1, and a decreased amount of TGFβR2, with an effective amount of TGFβ, such as to commit said MSC to further differentiation in the chondrocytic lineage.

11. The method according to claim 10, wherein the amount of TGFβR2 and/or the amount of Activin A receptor, type II-like 1 (ACVRL1) of the MSC or the population of MSCs is decreased by a method selected from the group consisting of gene knockdown of the expression of TGFβR2 and/or ACVRL1, a change of expression of a gene regulator of TGFβR2 and/or ACVRL1, growth factor treatment, RNA interference, and any other method decreasing the amount of TGFβR2 and/or ACVRL1 of the MSC, and any combination thereof, and/or wherein the amount of TGFβR1 of the mesenchymal stromal cell (MSC) or a population of mesenchymal stromal cells (MSCs) is increased by a method selected from the group consisting of overexpression of a gene, a change of expression of a gene regulator, gene transfer, growth factor treatment and any other method increasing the amount of TGFβR1 of the MSC.

12. The method according to claim 10, wherein additionally, the amount of ACVRL1 is decreased to about 50% or less of the initial amount of ACVRL1 in the MSC or populations of MSCs.

13. The method according to claim 10, wherein the amount of ACVRL1 is decreased to essentially 0% of its expression level.

14. The method according to claim 10, wherein said amount of TGFβR1, of TGFβR2, and of ACVRL1 of the MSC or the population of the MSCs refers to the amount of mRNA of TGFβR1, of TGFβR2, and of ACVRL1, respectively, or to the amount of protein TGFβR1, of TGFβR2, and of ACVRL1 protein, respectively.

15. The method according to claim 10, wherein said ratio between TGFβR1 and TGFβR2 of the MSC or the population of the MSCs is a molar ratio.

16. The method according to claim 1, wherein the amount of TGFβR1 of the MSC or the population of MSCs is increased and/or the amount of TGFβR2 of the MSC or the population of MSCs is decreased such that the ratio between TGFβR1 and TGFβR2 of the MSC or the population of MSCs is within the range of 0.13 to 0.5.

17. The method according to claim 1, wherein the amount of TGFβR1 of the MSC or the population of MSCs is increased and/or the amount of TGFβR2 of the MSC or the population of MSCs is decreased such that the ratio between TGFβR1 and TGFβR2 of the MSC or the population of MSCs is within the range of 0.135 to 0.3.

18. The method according to claim 1, wherein additionally, the amount of ACVRL1 is decreased to about 10% or less of the initial amount of ACVRL1 in the MSC or populations of MSCs.

19. The method according to claim 7, wherein in step d., determining if said ratio is within the range of 0.13 to 0.5.

20. The method according to claim 7, wherein in step d., determining if said ratio is within the range of 0.135 to 0.3.

21. The method according to claim 10, wherein in step b., increasing the amount of TGFβR1 and/or decreasing the amount of TGFβR2 of the mesenchymal stromal cell (MSC) or of the population of mesenchymal stromal cells (MSCs) such that the ratio between TGFβR1 and TGFβR2 of the MSC or the population of MSCs is 0.13 or higher.

22. The method according to claim 10, wherein in step b., increasing the amount of TGFβR1 and/or decreasing the amount of TGFβR2 of the mesenchymal stromal cell (MSC) or of the population of mesenchymal stromal cells (MSCs) such that the ratio between TGFβR1 and TGFβR2 of the MSC or the population of MSCs is 0.135 or higher.

23. The method according 10, wherein additionally, the amount of ACVRL1 is decreased to about 10% or less of the initial amount of ACVRL1 in the MSC or populations of MSCs.

* * * * *